(12) United States Patent
Palatzky et al.

(10) Patent No.: US 7,573,055 B2
(45) Date of Patent: Aug. 11, 2009

(54) APPARATUS FOR EMITTING LINEAR LIGHT

(75) Inventors: Roland Palatzky, Neusaess (DE); Robert Struschek, Kaufering (DE)

(73) Assignee: Texmag GmbH Vertriebsgesellschaft, Thaiwil ( * ) Notice: Subject to any disclaimer, the term of this patent is extended or adjusted under 35 U.S.C. 154(b) by 113 days.

(21) Appl. No.: 11/680,377

(22) Filed: Feb. 28, 2007

(65) Prior Publication Data

US 2007/0217197 A1    Sep. 20, 2007

(30) Foreign Application Priority Data

Mar. 1, 2006    (DE) ................. 10 2006 009 444

(51) Int. Cl.
*G01N 21/86* (2006.01)
*F21V 21/00* (2006.01)

(52) U.S. Cl. ................ 250/559.36; 362/249

(58) Field of Classification Search ........... 250/559.36, 250/239; 362/223–225, 294–296, 249, 364–369; 347/233–241
See application file for complete search history.

(56) References Cited

U.S. PATENT DOCUMENTS

| | | | |
|---|---|---|---|
| 3,368,071 A * | 2/1968 | Bentzman .............. 362/218 |
| 3,654,471 A | 4/1972 | Nilsson | |
| 3,869,606 A * | 3/1975 | Fordsmand ............ 362/218 |
| 4,876,633 A | 10/1989 | Engel | |
| 4,941,072 A * | 7/1990 | Yasumoto et al. ....... 362/249 |
| 5,032,960 A * | 7/1991 | Katoh .................. 362/240 |
| 5,274,243 A * | 12/1993 | Hochgraf ............. 250/559.41 |
| 5,504,516 A * | 4/1996 | Bax .................... 347/238 |
| 5,607,227 A * | 3/1997 | Yasumoto et al. ....... 362/249 |
| 6,082,870 A * | 7/2000 | George ................. 362/146 |
| 6,561,690 B2 | 5/2003 | Balestriero et al. | |
| 6,658,225 B2 * | 12/2003 | Thompson et al. ...... 399/128 |
| 6,659,623 B2 * | 12/2003 | Friend ................. 362/249 |
| 6,880,952 B2 | 4/2005 | Kiraly et al. | |

(Continued)

FOREIGN PATENT DOCUMENTS

DE    37 09 500 A1    10/1988

(Continued)

*Primary Examiner*—Stephen Yam
*Assistant Examiner*—Jennifer Bennett
(74) *Attorney, Agent, or Firm*—Fish & Richardson P.C.

(57) ABSTRACT

The apparatus for emitting light according to the present disclosure can include one or more linearly arranged devices for radiating light and one or more optical components which can be inserted into extruded profile. The extruded profile can be configured as hollow in an exemplary embodiment and can have an exit aperture for the egress of light from the extruded profile. The extruded profile can advantageously be configured in one piece, thereby permitting much easier assembly. Finally, the effect can also be achieved that dirt particles are not able to get into the carrier structure as readily, since a one-piece extruded profile has apertures that must be sealed only on one of its long sides and at its ends. The extruded profile can be used for different lighting tasks. The light-radiating devices can be inserted in variable positions in slots inside the extruded profile. In addition, the ideal optical components can be chosen and inserted in positions provided for them. This can make for a modular system that can be used in many different ways without the need to adapt or replace either the extruded profile or the inserts (the light-radiating devices and the other optical components).

14 Claims, 4 Drawing Sheets

U.S. PATENT DOCUMENTS

| | | | |
|---|---|---|---|
| 6,932,494 B1 * | 8/2005 | Burnett et al. | 362/287 |
| 2002/0036908 A1 * | 3/2002 | Pederson | 362/545 |
| 2002/0114155 A1 | 8/2002 | Katogi et al. | |
| 2005/0117336 A1 | 6/2005 | Jenny | |
| 2005/0122742 A1 | 6/2005 | Ho | |
| 2005/0128751 A1 * | 6/2005 | Roberge et al. | 362/276 |
| 2005/0158687 A1 | 7/2005 | Dahm | |
| 2006/0151725 A1 * | 7/2006 | Kim | 250/559.01 |

FOREIGN PATENT DOCUMENTS

| | | |
|---|---|---|
| DE | 42 10 445 | 10/1993 |
| DE | 42 10445 A1 | 10/1993 |
| DE | 203 19 640 U1 | 4/2004 |
| EP | 0 272 681 A2 | 6/1988 |
| EP | 0272 681 B1 | 6/1995 |
| WO | WO 2004/006560 A | 1/2004 |

* cited by examiner

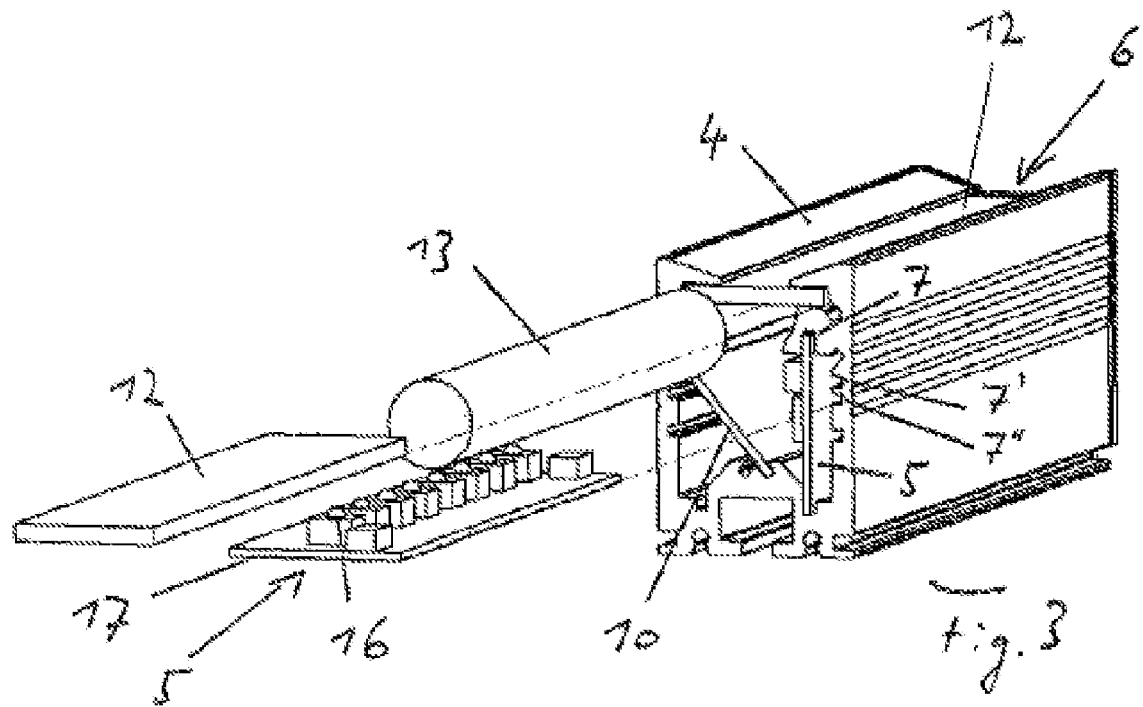
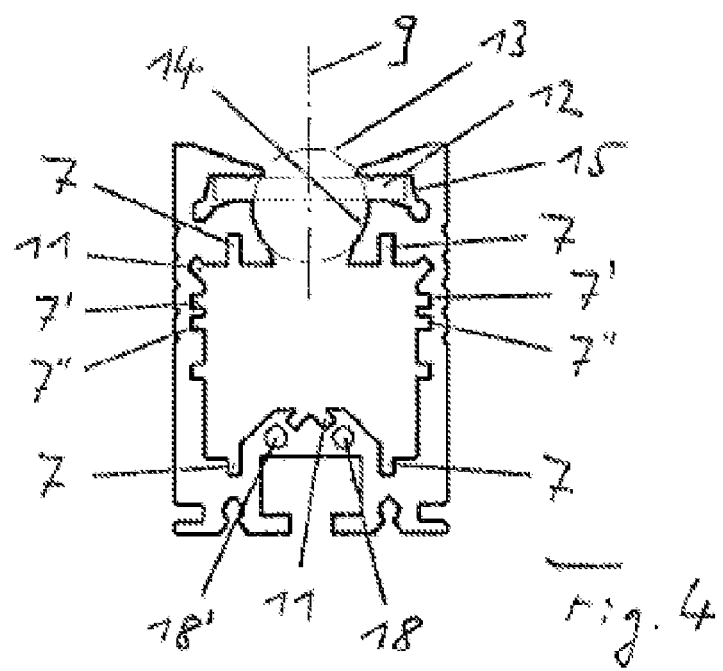

APPARATUS FOR EMITTING LINEAR LIGHT

CROSS-REFERENCE TO RELATED APPLICATION

Under 35 U.S.C. §119, this application claims the benefit of German patent application serial number 10 2006 009 444.1, filed Mar. 1, 2006, the contents of which are hereby incorporated by reference.

FIELD OF THE INVENTION

The present disclosure relates to an apparatus for emitting light, including linearly arranged devices for radiating light. The present disclosure also relates to a measuring arrangement including such an apparatus for emitting light and one or more cameras, and to a system for monitoring and measuring the edges of, or for detecting defects and/or irregularities in, a web of material being conveyed along a measurement plane.

BACKGROUND

The prior art includes systems for detecting defects and/or irregularities on a web of material being conveyed along a measurement plane that are equipped with a device for emitting linear light. The term "linear light" is understood here to mean bundled light that produces an illuminated line on the web of material, with the line usually running transversely to the web. Such a system can be used for example to examine a web of paper that is being conveyed along the measurement plane at high speed, one or more line scan cameras preferably being used in the reflected light method or the transmitted light method to pinpoint the edges of the web or defects and/or irregularities (e.g. thin spots, the inclusion of flies or dirt particles, etc.) by detecting brightness differences on the web of material. In the reflected light method, both the emission apparatus and the camera are disposed on the same side of the web of material, and in the transmitted light method they are on different sides of the web.

Apparatuses for emitting linear light are known for example from WO 2004/006560 and from U.S. Pat. No. 6,880,952 B2.

An object of the present disclosure is to create an apparatus for emitting linear light and thus a measuring arrangement which are of compact and robust construction. A further aim is to be able to obtain as many illumination variants as possible with one apparatus.

SUMMARY

The object is achieved by means of an apparatus according to claim 1. The dependent claims contain advantageous configurations.

The apparatus for emitting light according to the present disclosure includes one or more linearly arranged devices for radiating light and one or more optical components, which are arranged in a carrier structure. According to the disclosure, the carrier structure includes an extruded profile in which the devices for radiating light and the optical component or optical components are arranged.

The extruded profile is preferably configured as hollow and has an exit aperture for the egress of light from the extruded profile. The extruded profile can advantageously be configured as one piece, thereby permitting much easier assembly. Finally, the effect is also achieved that dirt particles are not able to get into the carrier structure as readily, since a one-piece extruded profile has apertures that must be sealed only on one of its long sides and at its ends.

The extruded profile preferably includes slots or other fastening devices into which the light-radiating devices and the optical component or the optical components can be inserted to arrange them inside the extruded profile. Very compact and robust construction is obtained in this way. The slots hold the light-radiating devices and the optical components securely in the intended placement, with essentially no need for additional fastening devices apart from fastening devices to effect longitudinal positioning inside the extruded profile.

According to a further aspect of the disclosure, the light-radiating devices can be arranged inside the extruded profile at at least two positions in a cross-sectional plane of the extruded profile. To this end, slots can be arranged inside the extruded profile so as to be able to arrange the light-radiating devices at at least two different distances from the light exit aperture of the extruded profile. This achieves the effect that the arrangement of the light-radiating devices can be adapted to the ideal geometric conditions in relation to the other optical components and to the measurement plane. It should be noted in this regard that this aspect does not presuppose the use of an extruded profile; rather, this variability can be obtained with other carrier structures as well.

The arrangement of the light-radiating devices can also be provided to be variable with respect to angular position. To this end, slots or other fastening devices can be arranged inside the extruded profile so that the light-radiating devices can be arranged in at least two different angular positions relative to the main radiation direction of the light from the extruded profile. The slots for the different angular positions are preferably arranged in the extruded profile such that the main radiation direction of the light-radiating devices can optionally be at 0° or 90° to the main radiation direction of the light from the extruded profile (hereinafter referred to as the "angular difference").

If the angular difference is 90°, the optical path from the light-radiating devices to the light exit aperture can be extended on out of the extruded profile, especially if the light-radiating devices are arranged so that they are closely adjacent one side of the extruded profile. Other angular differences may also be provided; however, an angular difference of 90° is a good choice for extruded profiles of approximately rectangular cross section.

In terms of the variability of the apparatus as a whole, if the light-radiating devices are arranged such that a given angular difference is provided, then a mirror plate, a scattering mirror plate or a reflective matte glass plate should also be provided in order to reflect the light emitted by the light-radiating devices in such a way that the light exits the extruded profile, i.e., the long-side exit aperture of the extruded profile, in the intended main radiation direction of the light. To this end, suitable slots or fastening means can be provided in the extruded profile in order to arrange the mirror plate, the scattering mirror plate or the reflective matte glass plate inside the extruded profile.

According to a further aspect of the present disclosure, the extruded profile can be configured such that either an optical plate (for example an optically clear disk or a translucent matte disk) or a rod lens can be disposed in the region of the long-side exit aperture of the extruded profile, optionally at the same position. The variability is increased still further in this way. Preferably provided for this purpose in the region of the exit aperture of the extruded profile are segment-of-a-circle-shaped surfaces, interrupted by slots, to be able to receive alternatively either a rod lens or an optical plate.

It becomes clear that one and the same extruded profile can be used for different lighting tasks. The light-radiating devices can be inserted in variable positions into slots inside the extruded profile. Moreover, the ideal optical components can be chosen and inserted in positions provided for them. This makes for a modular system that can be used in many different ways without the need to adapt or replace either the extruded profile or the inserts (the light-radiating devices and the other optical components).

The extruded profile can further be provided with ribs or other fastening means for securing a calibration unit, which can be used to adjust the camera(s) when the camera system is activated.

According yet another aspect of the present disclosure, disposed along the optical path of the light, after the light-radiating devices—but at a distance from the exit aperture of the light from the extruded profile—is a scattering mirror plate or a reflective matte glass plate that scatteringly reflects the bulk of the incident light in a relatively small angular region around the incident angle of reflection. The term "scattering reflection" herein means that no reflection of the kind produced by an ordinary mirror is to be obtained, but instead that a scattering cone is to exist around the incident angle of reflection. The scattering mirror plate of the present disclosure is therefore preferably a plate with an aluminum-bronze coating, a plate with a matte surface (for example a matte-white surface), a plate with a coating of matte barite or a plate with a beaded coating. This achieves the effect that scattering of the light takes place right inside the extruded profile, so the light is already very uniform when it exits the extruded profile.

This aspect of the disclosure is of importance for example with the use of electro-optical elements or LEDs that are essentially only point light sources—even if they are arranged along a line—so uniform linear light is not generated a priori. It should be pointed out that this aspect, as well, does not presuppose the use of an extruded profile; rather, this measure for generating more uniform linear light can also be implemented with other carrier structures.

A clear optical disk, a translucent matte disk, or a diffuser or rod lens can be arranged in the region of the exit aperture of the light from the extruded profile. The choice of a suitable optical component depends in particular on whether the preference is for high light output or very uniform illumination. For example, in the transmitted light method a high light output tends to be preferred, whereas in the reflected light method uniform illumination tends to be preferred. Inverse conditions may also be desired, however, depending on the application.

According to the present disclosure, the light-radiating devices preferably each include a circuit board on which preferably electro-optical elements or LEDs or other illuminating means are linearly arranged. The circuit boards can advantageously be constructed in modular fashion, in such a way that the overall length of the light-radiating devices depends on the number and respective lengths of the serially assembled circuit boards. Assuming an extruded profile for example 1000 mm long, a line of light with a width of 150 mm, 300 mm, 450 mm, 600 mm, 750 mm or 900 mm can be generated, depending on the circuit boards that are inserted. Depending on the measurement task, therefore, only the actual required area can be variably illuminated, it being possible to use the same extruded profile for this purpose. For other measurement tasks, lines of light for example 1500 mm wide can be generated with a longer extruded profile.

For purposes of this modularity, the light-radiating devices advantageously include pluggable connectors at the respective adjacent edges, so that all the light-radiating devices can be supplied with current and/or controlled via connecting lines from one side of the extruded profile. In addition, the light-radiating devices can be interrupted by an interposed insert, which is connected via pluggable connectors to the adjacent light-radiating devices, so that all the light-radiating devices can be supplied with current and/or controlled via connecting lines from one side of the extruded profile. Such an interposed insert is advantageous when for example only the edges of a web of material are to be illuminated, but not necessarily the central area of the web. In this case, the interposed insert merely serves as a pluggable connector or as a spacer between the light-radiating devices disposed in the respective edge regions of the extruded profile.

The light intensity basically decreases at an end of the linearly illuminated area, since smaller overlap effects are present in the end regions. To offset this effect, it can be provided according to the disclosure that in the case of light-radiating devices arranged at the edge of the extruded profile, the interspacing of the electro-optical elements or LEDs becomes continuously smaller toward the edge in order to obtain uniform illumination in the edge regions as well. Alternatively or cumulatively, it can be provided that the electro-optical elements or LEDs radiate a higher light output toward the edge in order to obtain uniform illumination in the edge regions as well.

According to yet another aspect of the present disclosure, one or more inner conduits can be provided in the extruded profile so that a coolant for dissipating heat can be routed therethrough. At least two inner conduits, connected to each other by an end piece at one end of the extruded profile, can be provided for this purpose, so that a first inner conduit can be used as a supply line and a second inner conduit as a discharge line for the coolant. The conduits are therefore advantageously connected to an apparatus for supplying coolant at only one end of the extruded profile.

Instead of inner conduits, an elongated pipe bent into a U shape at one end can alternatively be provided inside the extruded profile. The two arms of such a U-shaped pipe rest against inner, mutually confronting surfaces of the extruded profile, the inner surfaces being adapted to the shape of the U-shaped pipe to bring about increased heat conduction to the pipe.

Finally, cooling fins can alternatively or cumulatively be provided on an outer face of the extruded profile to effect simple but efficient cooling.

A measuring arrangement according to the present disclosure consists of an above-described apparatus for emitting light and one or more cameras, especially line scan cameras, both the emission apparatus and the camera or cameras being oriented toward a measurement plane.

A system according to the present disclosure for monitoring the web edges or for detecting defects and/or irregularities on a web of material being conveyed along a measurement plane includes such a measuring arrangement and an evaluation unit for analyzing data from the camera or cameras, in order to pinpoint defects and/or irregularities or to monitor web edge positions of the web of material or the web width thereof.

The present disclosure is explained below on the basis of preferred embodiments with reference to the appended drawings.

BRIEF DESCRIPTION OF THE FIGURES

FIG. 3 shows an extruded profile for an apparatus for emitting linear light according to an embodiment of the present disclosure, provided with different possible inserts;

FIG. 4 shows a cross section of an extruded profile for an apparatus for emitting linear light according to an embodiment of the present disclosure;

DETAILED DESCRIPTION

Figure 1:
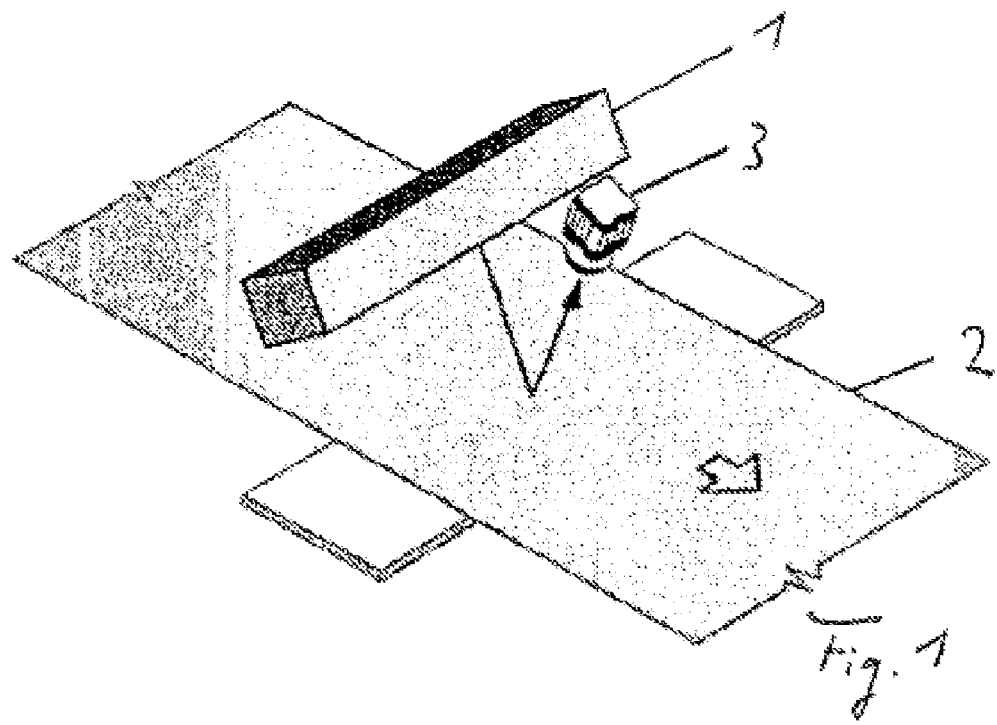
FIG. 1 shows a system for monitoring the web edges or for detecting defects and/or irregularities on a web of material by the reflected light method, including an apparatus for emitting linear light according to an embodiment of the present disclosure.

FIG. 1 shows a system for monitoring the web edges or for detecting defects and/or irregularities on a web of material by the reflected light method, including an apparatus 1 for emitting linear light according to one embodiment of the present disclosure. The apparatus produces on a web 2 of material of a linear light, i.e. a bundled light, which creates on the web 2 of material an illuminated line running transversely to the web 2 of material. With a system of this kind, for example a web of paper conveyed at high speed along the measurement plane can be examined, using at least one line scan camera 3, to identify defects and/or irregularities by the reflected light method or the transmitted light method by detecting brightness differences on the web of material.

Figure 2:
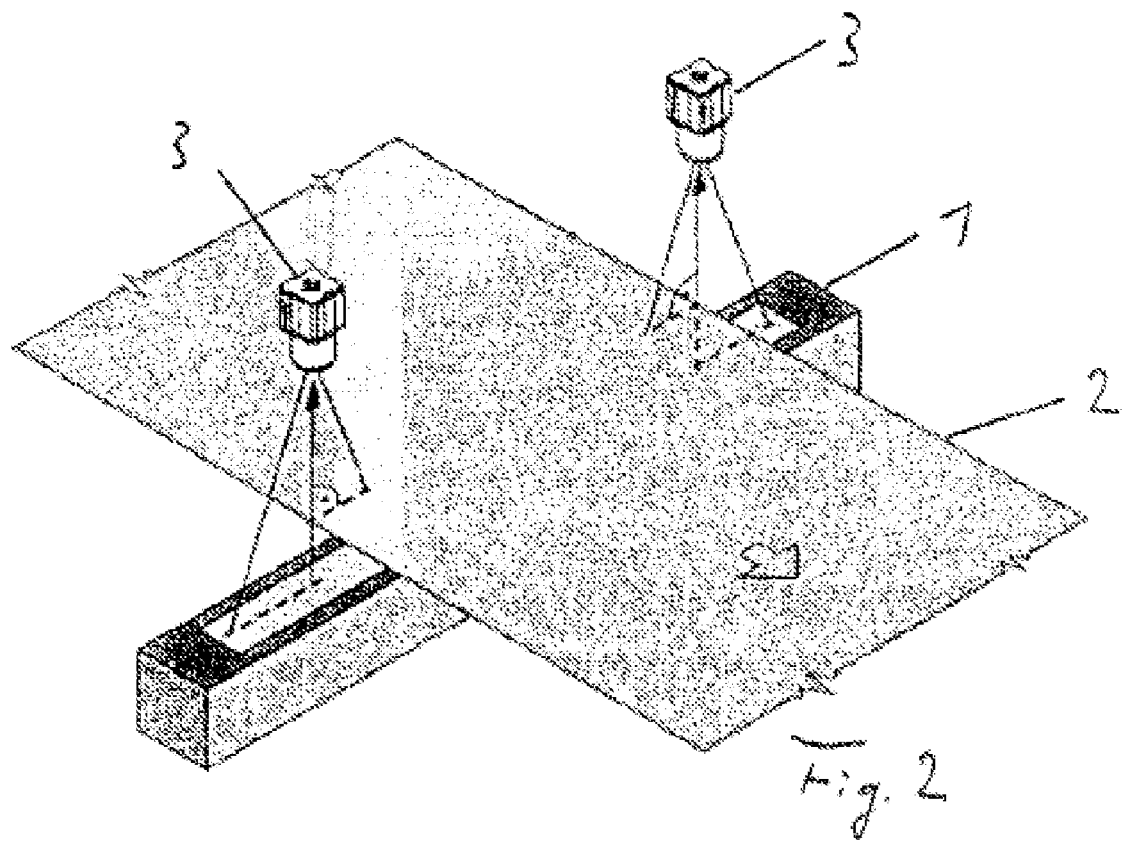
FIG. 2 shows a system for monitoring the web edges or for detecting defects and/or irregularities on a web of material by the transmitted light method, including an apparatus for emitting linear light according to a further embodiment of the present disclosure.
Figure 5:
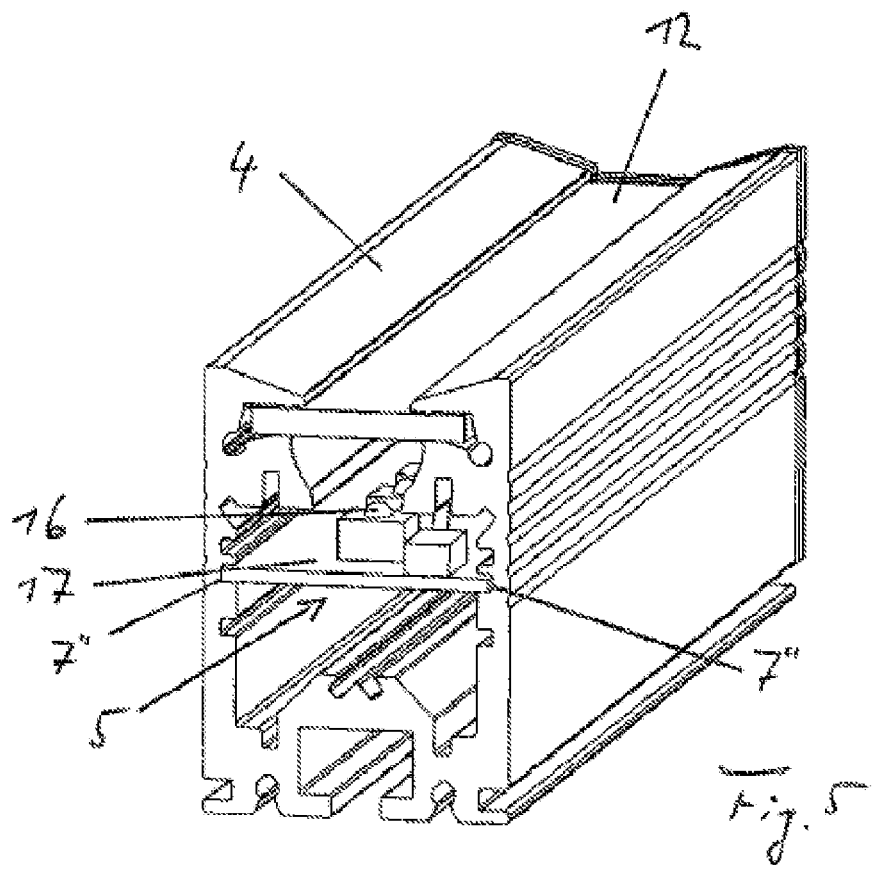
FIG. 5 shows an extruded profile for an apparatus for emitting linear light according to an embodiment of the present disclosure, provided with a first variant of possible inserts.

The apparatus 1 for emitting linear light can also be used for the transmitted light method. FIG. 2 shows a system for monitoring the web edges or for detecting defects and/or irregularities on a web of material by the transmitted light method, including an inventive apparatus 1 according to a further embodiment of the present disclosure. The apparatus 1 is disposed under the web 2 of material and beams linear light upward in the direction of two cameras 3.

FIG. 3 shows an extruded profile 4—preferably made of aluminum—for an apparatus for emitting linear light according to one embodiment of the present disclosure, provided with possible inserts. FIGS. 5 to 8 show the extruded profile 4 according to the same embodiment, provided with four different variants of possible inserts or possible arrangements of the inserts inside the extruded profile.

The apparatus for emitting light according to the present disclosure includes one or more linearly arranged devices 5 for radiating light and one or more optical components, which are inserted into the extruded profile 4. The extruded profile 4 is configured as hollow in the exemplary embodiment and has an exit aperture 6 for the egress of light from the extruded profile 4. The extruded profile can advantageously be configured as one piece, thereby permitting much simpler assembly. Finally, this also achieves the effect that dirt particles are not able to get into the carrier structure as readily, since a one-piece extruded profile has apertures that must be sealed only on one of its long sides and at its ends.

In the exemplary embodiment shown, the extruded profile 4 includes slots 7, 7' and 7" into which the light-radiating devices 5 and the optical component or the optical components can be inserted to arrange them at different possible positions inside the extruded profile 4. Very compact and robust construction is obtained in this way. The slots 7, 7' and 7" hold the light-radiating devices and the optical components securely in the intended placement, with essentially no need for additional fastening devices apart from fastening devices to effect longitudinal positioning inside the extruded profile.

Figure 7:
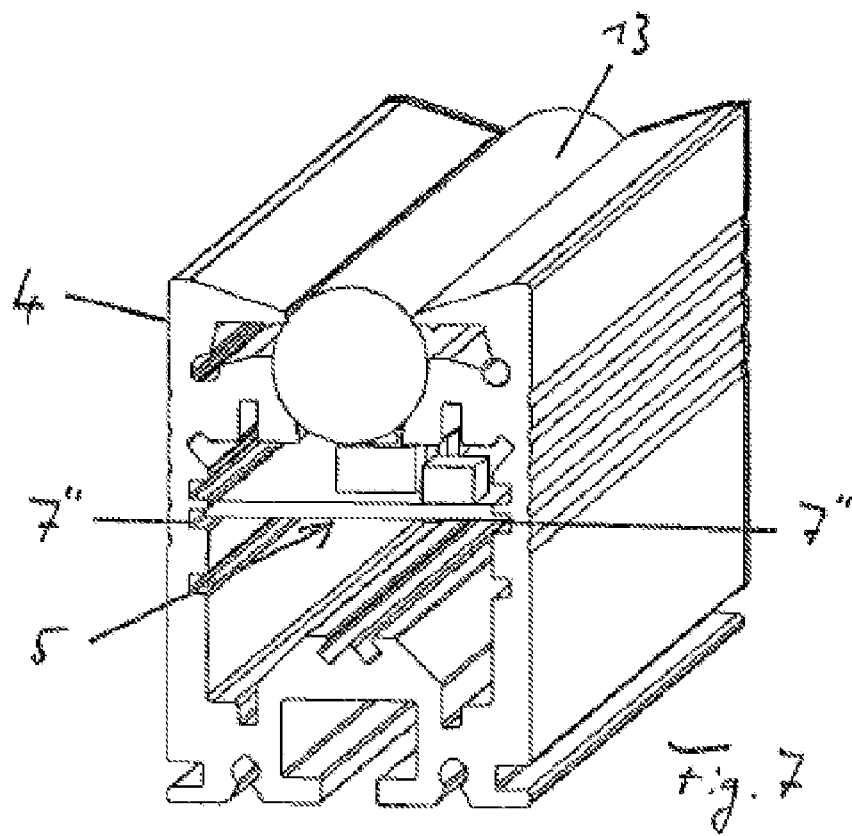
FIG. 7 shows an extruded profile for an apparatus for emitting linear light according to an embodiment of the present disclosure, provided with a third variant of possible inserts.
Figure 8:
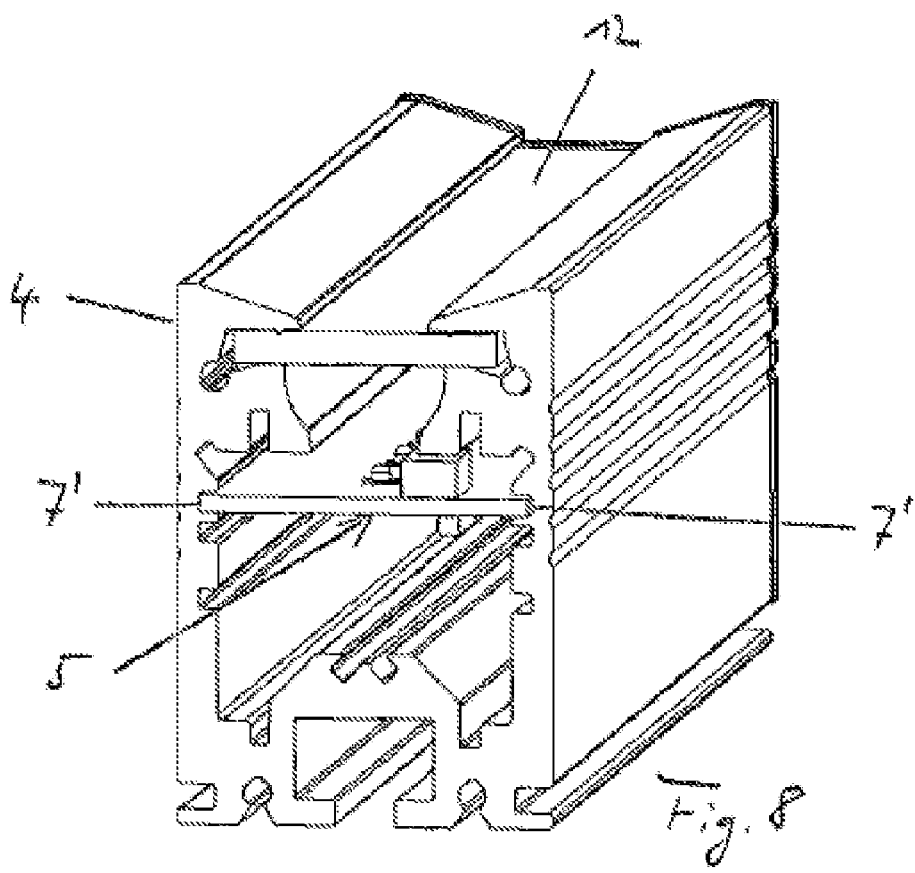
FIG. 8 shows an extruded profile for an apparatus for emitting linear light according to an embodiment of the present disclosure, provided with a fourth variant of possible inserts.

The slots 7' and 7" are arranged inside the extruded profile such that the light-radiating devices can be arranged at at least two different distances from the light exit aperture 6 of the extruded profile (cf. FIG. 7 versus FIG. 8). For this purpose, the distance between the confronting slots for the position denoted as 7' is identical to the distance between the confronting slots for the position denoted as 7", so that the same circuit board 17 for a light-radiating device can be inserted at both positions. This achieves the effect that the arrangement of the light-radiating devices can be adapted to the ideal geometric conditions relative to the other optical components and relative to the measurement plane, i.e. the web 2 of material.

In the exemplary embodiment, the arrangement of the light-radiating devices is also provided to be variable with respect to angular position. To this end, the slots 7 are arranged inside the extruded profile so that the light-radiating devices can be arranged in two different angular positions relative to the main radiation direction of the light from the extruded profile. The slots 7, 7' and 7" are arranged for this purpose in the extruded profile such that the main radiation direction 8 of the light-radiating devices 5 can discretionarily be at 0° or 90° to the main radiation direction 9 of the light from the extruded profile (see FIG. 6 for the angular difference of 90°). For this purpose, the distance between the confronting slots for the position denoted as 7 (FIG. 6) is identical to the distance between the confronting slots for the positions denoted as 7' (FIG. 8) or 7" (FIG. 7), so that the same circuit board 17 for a light-radiating device can be inserted variably at all these positions.

Figure 6:
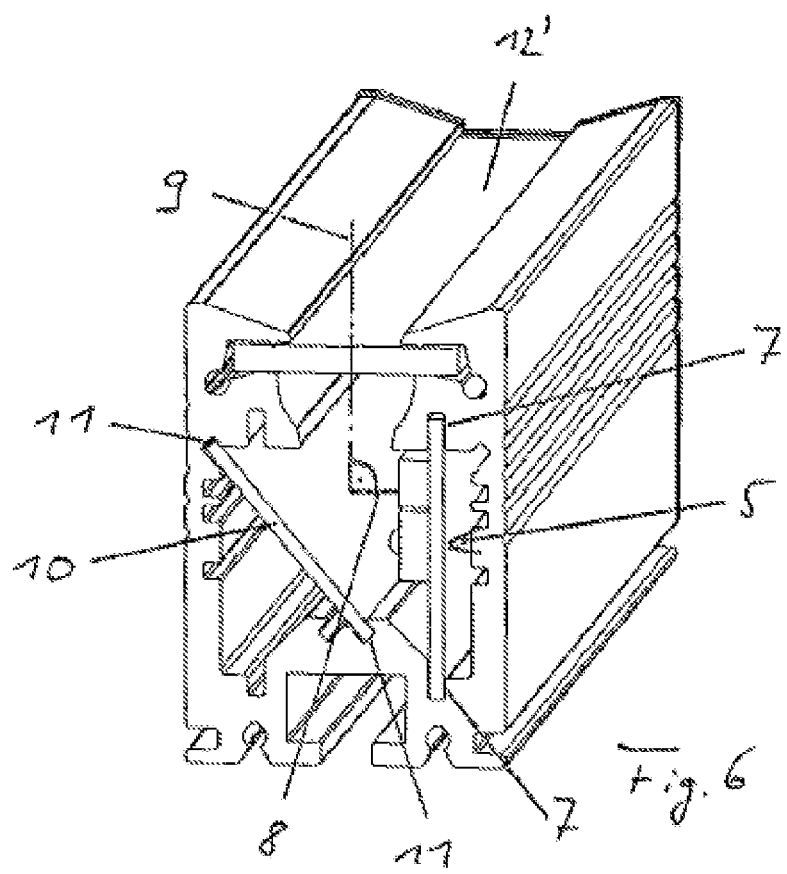
FIG. 6 shows an extruded profile for an apparatus for emitting linear light according to an embodiment of the present disclosure, provided with a second variant of possible inserts.

If the angular difference is 90°, as in the exemplary embodiment depicted in FIG. 6, the optical path from the light-radiating devices to the light exit aperture can be extended on out of the extruded profile, especially if the light-radiating devices are arranged so that they are closely adjacent one side of the extruded profile (FIG. 6, on the right). Other angular differences can also be provided; however, an angular difference of 90° is a good choice for extruded profiles of approximately rectangular cross section.

In terms of the variability of the apparatus as a whole, if the light-radiating devices 5 are arranged such that a given angular difference is provided, then a mirror plate, a scattering mirror plate 10 or a reflective matte glass plate should also be provided in order to reflect the light emitted by the light-radiating devices in such a way that the light exits the extruded profile in the intended main radiation direction 9 of the light. To this end, suitable slots 11 or fastening means can be provided in the extruded profile in order to arrange the mirror plate, the scattering mirror plate 10 or the reflective matte glass plate inside the extruded profile.

According to a further aspect of the present disclosure, the extruded profile can be configured such that either an optical plate 12 (for example an optically clear disk or a translucent matte disk) or a rod lens 13 can be arranged in the region of the long-side exit aperture 6 of the extruded profile, optionally at the same position (cf. FIG. 4). The variability is increased still further in this way. Preferably provided for this purpose in the region of the exit aperture 6 of the extruded profile are circular-segment-shaped surfaces 14 that are interrupted by slots 15, to be able to receive alternatively either a rod lens 13 or an optical plate 12.

If a rod lens 13 is used, the hollow space of the extruded profile 4 can be sealed by placing a rubber seal in each of the slots 15 during assembly. This sealing by means of rubber seals can also be provided if optical plates are used, the rubber seals then being configured as proportionately smaller.

It becomes clear that one and the same extruded profile can be used for different lighting tasks. The light-radiating devices can be inserted in variable positions into slots 7, 7' and 7" inside the extruded profile. Moreover, the ideal optical components can be chosen and inserted in positions provided for them. This makes for a modular system that can be used in many different ways without the need to adapt or replace either the extruded profile or the inserts (the light-radiating devices and the other optical components).

According to yet another aspect of the present disclosure, disposed along the optical path of the light, after the light-radiating devices 5—but at a distance from the exit aperture 6 of the light from the extruded profile—is a scattering mirror plate 10 or a reflective matte glass plate that scatteringly reflects the bulk of the incident light in a relatively small angular region around the incident angle of reflection. The term "scattering reflection" here means that no reflection of the kind produced by an ordinary mirror is to be obtained, but instead that a scattering cone is to exist around the incident angle of reflection. The scattering mirror plate of the present disclosure is therefore preferably a plate with an aluminum-bronze coating, a plate with a matte surface (for example a matte-white surface), a plate with a coating of matte barite or a plate with a beaded coating. This achieves the effect that scattering of the light is effected right inside the extruded profile, so the light is already very uniform when it exits the extruded profile.

This aspect of the disclosure is of importance for example with the use of electro-optical elements or LEDs 16 that are essentially only point light sources—even if they are arranged along a line—so uniform linear light is not generated a priori.

A clear optical disk 12', a translucent matte disk 12, or a diffuser or rod lens 13 can be arranged in the region of the exit aperture 6 of the light from the extruded profile. The choice of a suitable optical component depends in particular on whether the preference is for high light output or very uniform illumination. For example, in the transmitted light method a high light output tends to be preferred, whereas in the reflected light method uniform illumination tends to be preferred. Inverse conditions may also be desired, however, depending on the application.

According to the present disclosure, the light-radiating devices preferably each include a circuit board 17, on which preferably electro-optical elements or LEDs 16 are linearly arranged. The circuit boards 17 can advantageously be constructed in modular fashion in such a way that the overall length of the light-radiating devices 5 depends on the number and respective lengths of the serially assembled circuit boards 17. Assuming an extruded profile for example 1000 mm long, a line of light with a width of 150 mm, 300 mm, 450 mm, 600 mm, 750 mm or 900 mm can be generated, depending on the circuit boards that are inserted. Depending on the measurement task, therefore, only the actual required area can be variably illuminated, it being possible to use the same extruded profile for this purpose. For other measurement tasks, lines of light for example 1500 mm wide can be generated with a longer extruded profile.

For purposes of this modularity, the light-radiating devices 5 advantageously include pluggable connectors (not shown) at the respective adjacent edges, so that all the light-radiating devices can be supplied with current and/or controlled via connecting lines from one side of the extruded profile. In addition, the light-radiating devices 5 can be interrupted by an interposed insert (not shown), which is connected via pluggable connectors to the adjacent light-radiating devices, so that all the light-radiating devices can be supplied with current and/or controlled via connecting lines from one side of the extruded profile. Such an interposed insert is advantageous when for example only the edges of a web 2 of material are to be illuminated, but not necessarily the central area of the web. In this case, the interposed insert merely serves as a pluggable connector or as a spacer between the light-radiating devices disposed in the respective edge regions of the extruded profile.

The light intensity basically decreases at an end of the linearly illuminated area, since smaller overlap effects are present in the end regions. To offset this effect, it can be provided according to the disclosure that in the case of light-radiating devices arranged at the edge of the extruded profile, the interspacing of the electro-optical elements or LEDs 16 becomes continuously smaller toward the edge in order to obtain uniform illumination in the edge regions as well. Alternatively or cumulatively, it can be provided that the electro-optical elements or LEDs 16 yield a higher light output toward the edge in order to obtain uniform illumination in the edge regions as well.

According to yet another aspect of the present disclosure, one or more inner conduits 18, 18' can be provided in the extruded profile 4 so that a coolant for dissipating heat can be routed therethrough (see FIG. 4). At least two inner conduits 18, 18', connected to each other by an end piece (not shown) at one end of the extruded profile, can be provided for this purpose, so that a first inner conduit 18 can be used as a supply line and a second inner conduit 18' as a discharge line for the coolant. The conduits are therefore advantageously connected to an apparatus for supplying coolant at only one end of the extruded profile.

Instead of inner conduits, an elongated pipe or a tube (not shown) bent into a U shape at one end can alternatively be provided inside the extruded profile. The two arms of such a U-shaped pipe rest against inner, mutually confronting surfaces of the extruded profile, the inner surfaces being adapted to the shape of the U-shaped pipe to bring about increased heat conduction to the pipe.

Finally, cooling fins can alternatively or cumulatively be provided on an outer face of the extruded profile to effect simple but efficient cooling. A fan can also be provided in this case.

The invention claimed is:

1. An apparatus configured to emit light, comprising:
   one or more linearly arranged devices configured to radiate light;
   one or more optical components; and
   a carrier structure, the carrier structure comprising:
      an extruded profile;
   wherein the one or more linearly arranged devices and the one or more optical components are arranged in the extruded profile of the carrier structure;

wherein the extruded profile is hollow and comprises an exit aperture for the egress of light from the extruded profile; and wherein the extruded profile is configured such that the one or more linearly arranged devices can be arranged inside the extruded profile at two or more positions in a cross-sectional plane of the extruded profile; wherein the two or more positions comprise a first position and a second position; and wherein the first and second positions are at different distances from the exit aperture and the first and second positions are parallel to one another and to the exit aperture in the cross-sectional plane such that both respective main radiation directions of the one or more linearly arranged devices are toward the exit aperture and are at 0° to a main radiation direction of the light from the extruded profile when the one or more linearly arranged devices are arranged at the first position and at the second position; and wherein the extruded profile comprises slots into which the one or more linearly arranged devices and the one or more optical components can be inserted in order to arrange them inside the extruded profile; wherein the slots are arranged inside the extruded profile so as to be able to arrange the devices in two or more different angular positions relative to the main radiation direction of the light from the extruded profile, wherein the two or more different angular positions comprise the first position and a third position, and wherein the slot for the third position is arranged in the extruded profile such that the main radiation direction of the one or more linearly arranged devices when in the third position is at 90° to the main radiation direction of the light from the extruded profile.

2. The apparatus as in claim 1, wherein the extruded profile is configured as one piece.

3. The apparatus as in claim 1, wherein the extruded profile is configured such that either an optical plate or a rod lens can be arranged in the region of the exit aperture of the extruded profile.

4. The apparatus as in claim 1, wherein disposed in the region of the exit aperture of the extruded profile are circular-segment-shaped surfaces for receiving a rod lens, which are interrupted by slots so that they can alternatively receive an optical plate.

5. The apparatus as in claim 1, wherein slots or fastening means are provided in the extruded profile in order to arrange a mirror plate, a scattering minor plate or a reflective matte glass plate such that light emitted by the one or more linearly arranged devices is reflected in such a way that a main radiation direction of the reflected light coincides with the main radiation direction of the light from the extruded profile.

6. The apparatus as in claim 1, wherein arranged along the optical path of the light after the one or more linearly arranged devices but at a distance from the exit aperture of the light from the extruded profile is a scattering minor plate or a reflective matte glass plate that scatteringly reflects the bulk of the incident light in a relatively small angular region around the incident angle of reflection.

7. The apparatus as in claim 6, wherein the scattering mirror plate or the reflective matte glass plate is a plate with an aluminum-bronze coating, a plate with a matte surface, a plate with a coating of matte barite or a plate with a beaded coating.

8. The apparatus as in claim 1, wherein a clear optical disk, a translucent matte disk or a diffuser or rod lens is arranged in the region of the exit aperture of the light from the extruded profile.

9. The apparatus as in claim 1, wherein the one or more linearly arranged devices each comprise:
a circuit board; and
electro-optical elements or LEDs, the electro-optical elements or LEDs being linearly arranged on the circuit board.

10. The apparatus as in claim 9, wherein the circuit boards are constructed in modular fashion and serially assembled such that the overall length of the one or more linearly arranged devices depends on the number and respective lengths of the serially assembled circuit boards.

11. The apparatus as in claim 1, wherein one or more inner conduits are provided in the extruded profile so that a coolant for dissipating heat can be routed therethrough.

12. The apparatus as in claim 11, wherein at least two inner conduits are provided, which are connected to each other at one end of the extruded profile by an end piece, so that a first inner conduit can be used as a supply line and a second inner conduit as a discharge line for the coolant.

13. A measuring arrangement, comprising:
an apparatus configured to emit light according to claim 1; and
one or more cameras, wherein both the apparatus and the one or more cameras are oriented toward a measurement plane.

14. A system for monitoring web edges or web widths of a web of material, or for detecting at least one of defects or irregularities on the web of material, the web of material being conveyed along a measurement plane, comprising:
a measuring arrangement as in claim 13; and
an evaluation unit for analyzing the data from the one or more cameras, in order to detect the defects or the irregularities.

* * * * *

UNITED STATES PATENT AND TRADEMARK OFFICE
CERTIFICATE OF CORRECTION

PATENT NO. : 7,573,055 B2  
APPLICATION NO. : 11/680377  
DATED : August 11, 2009  
INVENTOR(S) : Roland Palatzky Page 1 of 1

It is certified that error appears in the above-identified patent and that said Letters Patent is hereby corrected as shown below:

Title Page, item 73
Assignee, Line 2, delete "Thaiwil" and insert -- Thalwil --.

Signed and Sealed this

Twenty-second Day of September, 2009

David J. Kappos
*Director of the United States Patent and Trademark Office*